United States Patent [19]

D'Alessio et al.

[11] Patent Number: 5,292,314
[45] Date of Patent: Mar. 8, 1994

[54] AUTOMATIC NEEDLE PROTECTOR

[75] Inventors: Larry M. D'Alessio, Manasquan, N.J.; John F. Romano, Washington Crossing, Pa.

[73] Assignee: International Medical Consultants, Inc., Washington Crossing, Pa.

[21] Appl. No.: 16,285

[22] Filed: Feb. 11, 1993

[51] Int. Cl.[5] .......................... A61M 5/32; A61M 5/00
[52] U.S. Cl. ...................................... 604/198; 604/263
[58] Field of Search ................ 604/110, 192, 198, 263

[56] References Cited

U.S. PATENT DOCUMENTS

| | | | |
|---|---|---|---|
| 4,723,943 | 2/1988 | Spencer | 604/198 |
| 4,801,295 | 1/1989 | Spencer | 604/198 |
| 4,911,693 | 3/1990 | Paris | 604/192 |
| 4,923,447 | 5/1990 | Morgan | 604/198 |
| 4,932,940 | 6/1990 | Walker et al. | 604/110 |
| 5,049,136 | 9/1991 | Johnson | 604/198 |
| 5,092,851 | 3/1992 | Ragner | 604/192 |
| 5,104,384 | 4/1992 | Parry | 604/192 |
| 5,169,392 | 12/1992 | Ranford et al. | 604/198 |
| 5,195,983 | 3/1993 | Boese | 604/110 |
| 5,201,708 | 4/1993 | Martin | 604/110 |

Primary Examiner—C. Fred Rosenbaum
Assistant Examiner—Frank Wilkens, III
Attorney, Agent, or Firm—Charles F. Gunderson; Paul J. Hayes; Judith C. Crowley

[57] ABSTRACT

A syringe has a needle mounted in the lower end of a tubular mount. A protective cover, in the form of a sleeve, fits over this lower end of the tubular mount, and extends to fully cover the sharp end of the needle. The tubular mount has a pair of elongated, axial slots for the entry and exit of a cog or lug on the inside of the sleeve. Pressure on the sleeve slides the lug up the entry slot and exposes the needle. A cross over slot carries the lug to the exit slot, where it slides down to the lower end of the mount, and over a locking ridge to automatically and securely recover the needle. A spring, coupled between the mount and the sleeve has an axial force urging the sleeve down in either slot, and a rotary force urging the cog towards the exit slot. The lug must be in the entry slot to depress and use the needle, but the lug is then rotated to the exit slot and returned by the spring, automatically, to lock the lug in the safe, covering position of the sleeve.

14 Claims, 1 Drawing Sheet

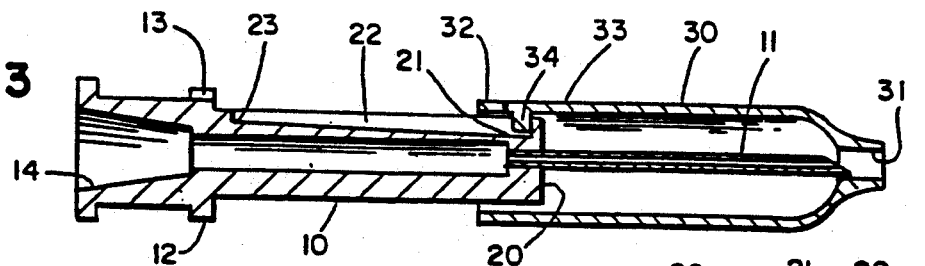
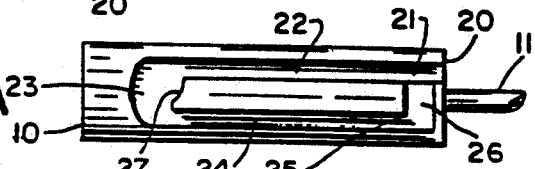
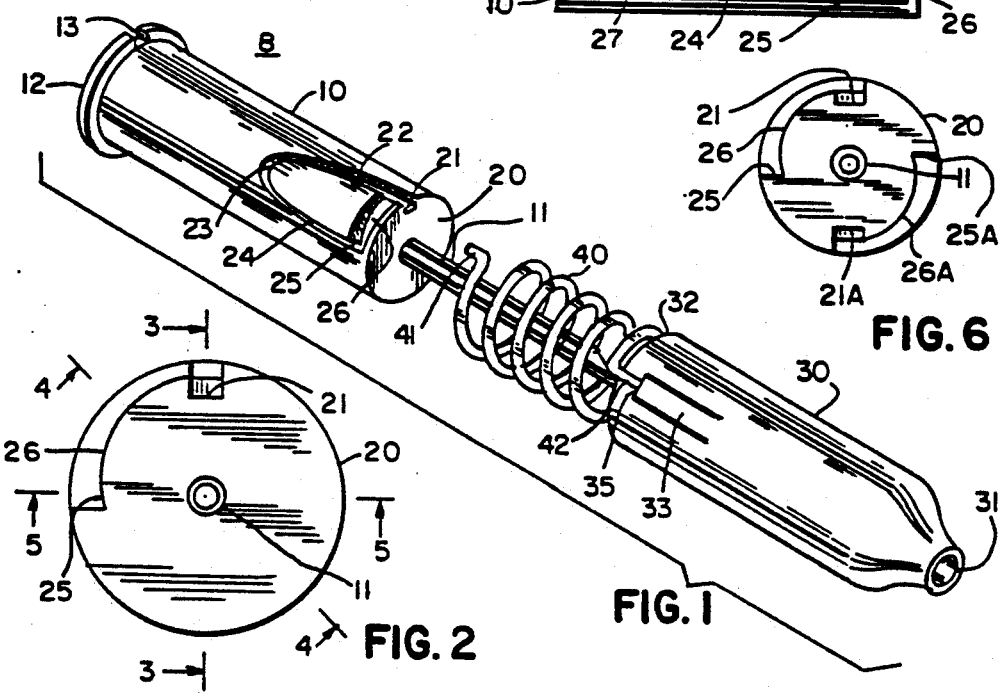
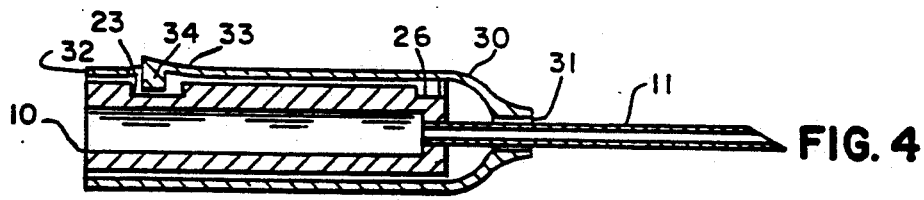
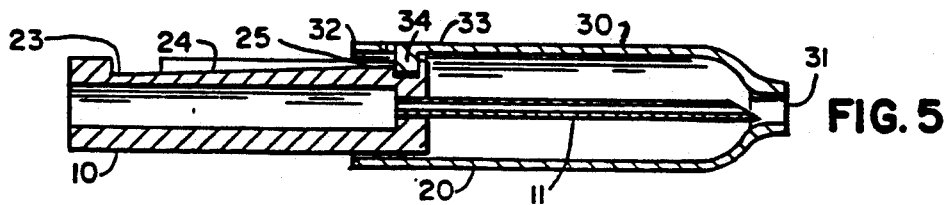

AUTOMATIC NEEDLE PROTECTOR

BACKGROUND OF THE INVENTION

The use of needles for penetrating the body is essential in modern medecine. Their uses include injecting fluids into, or drawing blood or other fluids out of almost any part of the body. The sizes of the needles, and the associated syringe equipment, will vary according to their function.

However, regardless of the size, use, or function, the needle is inevitably a sharp and potentially hazardous object. It should be safely stored, and, more important, safely discarded after any use. This is a mandatory at all health facilities, but the facts prove that, with human nature, and overworked, human hospital staffs, used needles will always be found, and will always be a potential hazard.

The potential danger in needles is, of course, in used needles that may have picked up a virus of some kind from anyone using, or being injected by a needle. Once used, the needle must be considered contaminated, and, even if the risk is microscopic, it is a potential threat to the next person who, accidentally or otherwise, comes in contact with the needle. With certain deadly viruses living in a few human beings today, no gamble, however microscopic, is tolerable.

All hospitals, and other users of needles, have established systems and rules for the control of the use of and disposition of needles. Most of these are almost foolproof, and restrict the use of needles to well trained professional personal. However, it is now these, valuable people who are at risk from the casual, unprotected needle that may have been accidentally overlooked, and just lying around. Contact with this needle could be equally unpredictable. One could be standing, sitting, or in motion of any kind, and the contact could be with any part of the body.

Again, the risk of a trained medical technician coming in contact with a stray needle—let along its sharp end—should be negligible, and, that this particular needle might be infected, would be another very-remote possibility, but, where that possibility, however remote, could be lethal, or harmful in any way, the stakes are still too high.

The obvious, and basic, solution to the problem would be to have a safety shield or cover over the needle, before and after it is used. This is done quite effectively in several of the systems, but, in most of the systems, it relies on the human function of putting on, taking off, and putting the safety shield back on before discarding the needle in the required manner.

What is needed is a safety shield that is part of the needle structure, and that is locked in a position that covers and protects the sharp end of the needle. There must be a means for uncovering the safety shield, and activating the device for use, at least one time, but the safety shield must be returned, automatically, to its locked, protective position immediately after use.

SUMMARY OF THE INVENTION

A surgical needle projects from the lower end of a tubular structure. A protective cover, or shield, in the form of a tubular sleeve, slightly larger than the tubular structure, has an upper end fitting over the lower end of the tubular structure. The lower end of the sleeve must completely cover and guard the sharp end of the needle. Elongated, generally axial, entrance and exit slots are formed in the tubular structure, between its lower and upper ends to engage a spring-loaded lug on the underside of the tubular sleeve. This allows the sleeve to move upward, with the lug sliding along the entrance slot of the tubular structure, to uncover the needle. The lug then rotates through a change-over slot, to the exit slot, to be forced downward and lock at the base of the exit slot, to recover and guard the needle. A spring connected between the tubular structure and the sleeve provides a radial torque to urge the lug from the entrance slot, through a change-over slot, toward the exit slot. The spring also provides an axial force to oppose the uncovering of the needle and to urge the sleeve, always, toward its needle-covering and locking position. The user end of the tubular structure will be provided with a luer, or other fitting to couple the needle assembly to its intended function.

BRIEF DESCRIPTION OF THE DRAWINGS

FIG. 1 shows an isometric, exploded view of the device;

FIG. 2 shows a plan view of the needle amount;

FIG. 3 shows a cross section of the device along the lines 3—3 of FIG. 2;

FIG. 4 shows a cross section of the device along the lines 4—4 of FIG. 2;

FIG. 4A shows a top view of the needle mount normal to the lines 4—4 of FIG. 2;

FIG. 5 shows a cross section of the device along the lines 5—5 of FIG. 2; and

FIG. 6 shows a plan view of another variation of the needle amount.

DETAILED DESCRIPTION OF THE INVENTION

Referring now more particularly to FIG. 1, an isometric view of the basic device 8 is shown in an exploded form to clearly illustrate the elements that interact to provide the automatic, safety, needle protector. An upper portion 10 is a hollow tubular mount that supports a needle 11 at one, lower end 20. The other, upper end has a flange 12, with a notch or slot 13 to accommodate the upper end 41 of a spring 40 in a manner that will be described later.

This other, upper end of the tubular sleeve 16 will, normally, include one of the conventional couplings for a syringe, such as the luer fitting 14 shown in FIG. 3. This has been omitted here, and in the other drawings, for simplicity. Other fittings for similar functions can also be accommodated.

The needle 11 is mounted in the center of the base 20 at the lower end of the tubular needle mount 10, in a well known manner. The sharp point, or tip, of the needle will be protected by a cover or sleeve 30.

This exploded view shows, quite clearly, typical slots in the needle mount that control the position and function of the protective cover 30 for the needle in a manner that will be illustrated in the other figures and described in more detail in due course.

These typical slots include an opening 21 for an elongated starting or entrance slot 22 that goes up to a change-over slot 23, that leads to an elongated exit slot 24 that ends in a locking ledge 25 that automatically locks the protective cover 30, with its lower end 31 over the needle.

The protective cover 30 has an opening 31 in its lower end that the needle can extend through when its inner lug 34 is moving through the slots 22, 23, and 24, and the device is in use. The other, upper end 32, as noted earlier, is open and forms the sleeve that fits loosely around the tubular needle mount 10. A notch 35 may be provided in the upper end 32 of the sleeve 30 to support the lower end 42 of the spring 40, as shown. This spring 40 provides the automatic operation of the protective cover.

Another, flat spring 33 actuates a lug or cam 34, seen in FIGS. 3, 4, and 5, that rides in the slots 21 through 26 for the automatic control of the protective sleeve.

The spring 40 would, in operation, fit loosely over the tubular needle mount 10. The upper end clip 41 would fit into, and may be secured in the notch or slot 13 of the flange 12. The lower end clip 42 would fit into the notch or slot 35, as noted earlier, and may also be secured therein.

FIG. 2 shows a plan view of the lower end 20 of the tubular needle mount, seen along the needle 11. This more clearly, shows the opening 21 for the start of the lug 34, mounted on the underside of the spring 33, through its automatic locking path. This also shows the ledge 25, at the end of the slot 24, that secures the lug or cog 34 and locks the protective cover 30, with its end 31 well over the sharp end of the needle. Actually, the needle can be reactivated by rotating the sleeve 30, and moving its cog up the ramp 26 to drop back into the starting slot at 21.

FIG. 3 shows a cross section of the device along the lines 3—3 of FIG. 2. This shows the protective sleeve 30 with its upper end 32 over the tubular mount 10, its lower end 31 covering and protecting the sharp end of the needle 11, and its cog 34 started in the opening 21. The slot 22 will guide the cog to the change-over slot 23, and may raise it partially in the process. This figure also shows the flange 12, with the notch or slot 13 to accommodate the upper, outer end clip 41 of the spring 40.

The spring 40 is not shown in this and the subsequent drawings for simplicity and clarity in illustrating the other, most important elements of the safety cover, and their complex functions.

A typical luer fitting 14 is illustrated in this figure. Obviously this—or a similar coupling—would be necessary for coupling this safety device to any conventional unit that needs a hypodermic needle, which is the normal function of this device.

FIG. 4 shows another cross section of this device along the lines 4—4 of FIG. 2. This shows the protective sleeve or cover 30 drawn to the upper end of the tubular mount 10. This shows the cog 34, on the flat spring 33 of the sleeve 30 in the cross-over slot 23, and the needle fully exposed. As in all of these figures, similar elements are similarly numbered. The luer fitting 14 is, again, omitted for simplicity in this and the rest of these drawings.

FIG. 4A is a top view of the tubular mount 10 for mounting the needle 11, normal to the lines 4—4 of FIG. 2, and is added to illustrate another variation of the slots 21 through 26. This is the version that is, actually, used in the drawings 3, 4, and 5. To this has been added a notch 27 along the cross-over 23. This would hold the lug 34 against the pressures of the spring and would allow the protective cover 30 to be held with the needle exposed, if necessary, while it is being inserted or used. Subsequent movement or use of the cover 30 would complete the cycle, along the path of the lug 34, to the slot 24 and to the ledge 25, to lock the protective cover 30 in its safe position.

This figure also shows more depth to the crossover 23. Actually this crossover could extend from near the top of the slots to near the lower end of the mount. This could provide the essential, automatic safety locking of the sleeve with a minimal penetration of the needle, which might be advisable in many cases.

FIG. 5 is another cross section of the device, along the lines 5—5 of FIG. 2, and this shows the protective cover at the end of its cycle, with the lug 34 of the protective cover system locked against the ledge 25, and the end of the cover 31 well over the tip of the needle 11.

This shows the cross-over slot 23 and the slot 24 with its ramp that carries the cog 34 up until it passes over the ledge 25, where the pressure of the spring 33 depresses the lug 34 to lock the safety shield in its safe condition. This spring 40, of course, in its axial pressure urges the cover and lug along the slot 24 to the locking position.

FIG. 6 is another plan view of the bottom 20 with a variation of the needle holder, again in line with the needle 11. This shows an additional slot 21A, a ledge 25A, and a resetting slope 26A to accommodate an additional lug, not shown, to double the strength and the safety of the automatic locking function. Additional combinations of slots and lugs could, obviously, be added for additional strength and safety.

In operation, the device would normally be assembled with the elements of FIG. 1 compressed to the profile of FIG. 3. For example, the spring 40 would fit loosely over the tubular needle mount 10, with its upper end 41 seated in the notch 13 of the mount. This holds the protective cover, or sleeve 30 with its outer end 31 covering the sharp end of the needle 11, and its inner end fitting over the lower end 20 of the tubular needle mount. The lower end of the spring 42 is secured into the slot 35 of the protective cover, to hold the cog 34, mounted in the cover, in line with and against the ledge 25 so that the protective cover cannot be pushed back to expose the sharp end of the needle, whether it has been used or not.

When it is time to use the needle, for any reason, the needle mount 10 can be coupled to an appropriate syringe, or other device at its fitting 14. The cover or sleeve 30 can then be rotated—in this case clockwise—to move the cam 34 up the slope 26 to drop into the opening 21 at the start of the slot 22. This puts a rotary torque on the spring 40 which urges the cam back to the angle of the slot 24, which leads back to its locking ledge 25. However, the only way the cam can get back from its starting position 21 is to slide along the slots 22, 23, and 24 to be lifted and dropped back into the locking position at 25.

In other words, once the protective cover or sleeve is armed or cocked, the spring exerts a rotary pressure on the cover to urge the cam back towards its exit slot 24, and its locking position at 25. The spring also exerts an axial pressure on the cover to hold it in position over the sharp end of the needle until it is being used. The spring is then compressed axially to expose the needle for use, while moving the cam along the slots 22 and 23. Then the cam can only follow the slot 24 to return the cam, automatically, by the combined rotary and axial pressures of the spring, to its safe, locking position over the ledge 25 where the sharp end of the now used needle is automatically and permanently protected against accidental penetration of anything or anybody.

The spring, here, has this double function, and insures the automatic operation of the safety protective cover. The spring may be made of any springy material, from metal to plastic, and may be of any suitable, functional shape. Actually, the spring 40 may be molded as part of the sleeve 30, when suitable materials are chosen.

The materials chosen would presumably be of plastic, both the protective cover, with or without the spring, and the tubular mount for the needle would, obviously, be molded for mass production and cost effectiveness. While the safety of medical workers is of prime importance, the cost of providing safety should be reasonable. The object of this invention is to provide the best possible, and almost fool-proof protection, at a minimal cost.

It should be noted that these units are disposable—as must all needle mounts be—but these are permanently protected whenever they are disposed. The law, of course, meticulously requires a very special disposal of all medical wastes, which means there is no problem. However, sadly, human error, indifference, or duplicity loads our beaches and other facilities with medical wastes.

The mount 10 that physically supports the needle, which is the essential element of this device, is standard, and similar to many standard needle holders, that couple a needle to a luer, or other fitting, for its ultimate use. However, this unit may be slightly longer to accommodate the motion of the protective sleeve over the needle and mount.

The length of the sleeve, and the mount, will vary with the length and size of the needle, which will vary according to its many uses. The size and shape of the device will vary, along with the ultimate use. This will, again, be a function of the size, and length of the needle. The smallest possible would, of course, be most desirable.

A solid, thin cap over the base 20, at the lower end of the mount would be very easy to attach, and desirable for locking the lug in both directions. This would prevent the sleeve from being pulled off the needle mount, as well as from being pushed in to expose the needle, which would virtually eliminate exposure of the needle in any manner. In this case, a secondary means for raising the spring 33 would be needed to fit the lug 34 in either the starting slot or the locking ledge.

This could also avoid the need for, or use of the slope 26, which could be eliminated, to avoid the accidental rotation of the sleeve to arm the device.

The protective sleeve 30, as well as most of the rest of the device, would be of plastic for ease of manufacture. The sleeve should be as small as practical, and quite transparent to allow the needle to be seen and controlled. The opening at 31 may be the full size of the sleeve, or may be just large enough, as shown, for the needle to fit through.

We claim:

1. A needle protector comprising a tubular needle mount, having a hypodermic needle mounted at its lower end; a protective sleeve of a slightly larger inner diameter than the diameter of said tubular needle mount; the upper portion of said sleeve fitting over said lower end of said mount, and the lower portion of said sleeve being open but extending beyond the sharp end of said needle to guard said needle; an entrance slot in a side of said mount extending upwards a given distance from said lower end of said mount; an exit slot in said side of said mount, substantially parallel with said entrance slot, extending downwards from said given distance to said lower end of said mount; a crossover slot in said side of said mount, at said given distance above said lower end, connecting the upper ends of said entrance and exit slots; a spring-loaded lug projecting inside of said upper portion of said sleeve to fit in and be guided by said slots in said mount; and a lower end connected to said upper portion of said sleeve; said spring supplying a rotary force to hold said lug in line with said exit slot, and an axial force to push said lug toward said lower end of said mount; an arming slot disposed between said lower ends of said exit and entrance slots to permit said sleeve to engage said lug in the beginning of said entrance slot upon rotation of said sleeve; means for depressing said spring axially to move said lug to said given distance from said entrance slot, to expose said needle for use, after which, said rotary force of said spring moves said lug along said crossover slot to said exit slot, whereat said axial force of said spring moves said lug down said exit slot to said lower end of said mount; and a ridge at said lower end of said exit slot to receive said lug, and lock said lug and said sleeve in a position to securely cover said needle; and means for coupling said upper end of said needle mount to any device requiring a needle.

2. A needle protector, as in claim 1, wherein said entrance and exit slots are sloped to raise said spring-loaded lug from full depth at the lower end of said entrance slot to near the surface of said mount at the lower end of said exit slot, to provide said ridge for said lug to fall into to lock said sleeve in a position to guard the sharp end of said needle.

3. A needle protector, as in claim 1, wherein said arming slot has an upward slope between said lower ends of said exit and entrance slots, to raise said lug out of said locking ridge and into the beginning of said entrance slot for using said needle.

4. A needle protector, as in claim 1, wherein said crossover slot extends substantially from said lower end of said mount to said upper end of said mount.

5. A needle protector, as in claim 1, further comprising additional entrance, exit, and crossover slots positioned around said sides of said mount to accommodate additional, corresponding, spring-loaded lugs, projecting inside of said upper portion of said sleeve to provide additional security to the locking of said sleeve.

6. A needle protector, as in claim 1, wherein a ledge is provided along a lower edge of said crossover slot to provide an intermediate resting place for said lug, moving from said entrance to said exit slot, to hold said lug, with said sleeve withdrawn and said needle exposed for precise injection before continuing its locking cycle.

7. A needle protector, as in claim 1, wherein the opening in said lower portion of said sleeve is only slightly larger than said needle, to provide better visibility and control of said needle.

8. A needle protector, as in claim 1, wherein all of the elements of the device, except the needle, are formed of transparent plastic, to provide the maximum visibility and control of the needle.

9. A needle protector, as in claim 1, wherein said means for connecting said needle mount to any device is a luer fitting.

10. A needle protector, as in claim 1, wherein said crossover slot extends from said given distance upward toward said upper end of said mount.

11. A needle protector comprising:

a needle;

a mount having an upper end to which a fitting is attached, said fitting adapted for coupling to a unit operative with said needle, a lower end to which said needle is attached, and a slot disposed in a side thereof; and a protective sleeve having a diameter larger than said mount, said protective sleeve having an upper end fitting over said lower end of said mount and an apertured lower end, wherein said sleeve is adapted for being in a protective position in which said lower end of said sleeve is disposed over said needle or a retracted position in which said needle is exposed through said apertured lower end of said sleeve, said sleeve having a lug for mating with said slot so that said sleeve is moved between said protective position and said retracted position as said lug moves through said slot;

wherein said slot comprises an entrance slot extending from said lower end of said mount toward said upper end of said mount, an exit slot extending from said upper end of said mount toward said lower end of said mount, said entrance slot and said exit slot in communication proximate said upper end of said mount;

said slot further comprising an arming slot extending between said exit slot and said entrance slot.

12. The needle protector recited in claim 11 wherein a spring is coupled between said upper end of said mount and said upper end of said sleeve, said spring providing a rotary force to move said lug through said slot and an axial force to move said lug toward said lower end of said mount.

13. The needle protector recited in claim 11 wherein a crossover slot extends between said entrance and exit slots from ends thereof distal from said lower end of said mount toward said upper end of said mount.

14. The needle protector recited in claim 11 wherein said slot further comprises a ridge disposed at said lower end of said mount for receiving said lug to maintain said sleeve in said protective position.

* * * * *